(12) United States Patent
Lu

(10) Patent No.: US 7,410,979 B2
(45) Date of Patent: Aug. 12, 2008

(54) SYNERGISTICALLY EFFECTIVE COMBINATIONS OF DIHALOACETAMIDE COMPOUNDS AND INTERFERON OR RIBAVIRIN AGAINST HCV INFECTIONS

(75) Inventor: Henry Lu, Foster City, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 352 days.

(21) Appl. No.: 10/993,212

(22) Filed: Nov. 19, 2004

(65) Prior Publication Data

US 2005/0129659 A1    Jun. 16, 2005

Related U.S. Application Data

(60) Provisional application No. 60/523,405, filed on Nov. 19, 2003.

(51) Int. Cl.
*C07D 213/02* (2006.01)
*A61K 31/44* (2006.01)

(52) U.S. Cl. .................. 514/332; 514/332; 514/333; 514/340; 514/342; 546/255; 546/256; 546/268.1; 546/269.7

(58) Field of Classification Search .................. None
See application file for complete search history.

(56) References Cited

U.S. PATENT DOCUMENTS

| | | | |
|---|---|---|---|
| 2,852,503 A | 9/1958 | Edward et al. | |
| 3,189,447 A | 6/1965 | Neugebauer et al. | |
| 3,257,203 A | 6/1966 | Klupfel et al. | |
| 3,335,149 A | 8/1967 | Preston | |
| 3,910,942 A | 10/1975 | Neidermyer et al. | |
| 3,964,896 A | 6/1976 | Neidermyer et al. | |
| 4,087,409 A | 5/1978 | Preston | |
| 4,405,793 A | 9/1983 | Fuchs et al. | |
| 4,743,521 A | 5/1988 | Hoffmann et al. | |
| 4,752,324 A | 6/1988 | Thomas et al. | |
| 4,777,258 A | 10/1988 | Sitzmann | |
| 5,151,441 A | 9/1992 | Mueller et al. | |
| 5,256,666 A | 10/1993 | Mueller et al. | |
| 5,463,071 A | 10/1995 | Himmelsbach et al. | |
| 5,814,627 A | 9/1998 | Schwab et al. | |
| 6,277,830 B1 | 8/2001 | Ganguly et al. | |
| 6,355,669 B1 | 3/2002 | Yamauchi et al. | |
| 6,403,564 B1 | 6/2002 | Ganguly et al. | |
| 6,579,880 B2 | 6/2003 | Weidner-Wells et al. | |
| 6,759,538 B2 | 7/2004 | Singh et al. | |
| 7,157,473 B2 * | 1/2007 | Singh et al. .................. | 514/332 |
| 7,220,745 B2 | 5/2007 | Singh et al. | |
| 2002/0035156 A1 | 3/2002 | Roniker et al. | |

FOREIGN PATENT DOCUMENTS

| | | | |
|---|---|---|---|
| CA | 2431171 | * | 6/2002 |
| CH | 392520 | | 10/1965 |
| CH | 559 195 | | 2/1975 |
| DE | 21 37 719 | | 2/1973 |
| DE | 27 21 955 | | 11/1978 |
| DE | 100 32 874 | | 1/2002 |
| DE | 101 48 598 | | 10/2002 |
| EP | 563686 | | 3/1993 |
| EP | 0 776 894 | | 6/1997 |
| EP | 92/7992 | | 7/1999 |
| EP | 1 180 518 | | 2/2002 |
| EP | 1 348 706 | | 10/2003 |
| FR | 1 459 375 | | 4/1966 |
| JP | 02-146048 | | 6/1990 |
| JP | 03-122652 | | 5/1991 |
| JP | 04124178 | | 4/1992 |
| JP | WO 02/46186 | * | 6/2002 |
| WO | 93/17671 | | 9/1993 |
| WO | 94/17059 | | 6/1994 |
| WO | 95/24397 | | 9/1995 |
| WO | 98/17652 | | 4/1998 |
| WO | 98/47509 | | 10/1998 |
| WO | 99/04390 | | 1/1999 |
| WO | 99/20309 | | 4/1999 |
| WO | 02/20436 | | 3/2000 |
| WO | WO 00/23454 | | 4/2000 |
| WO | 00/40242 | | 7/2000 |
| WO | 00/45799 | | 8/2000 |
| WO | 00/78726 | | 12/2000 |
| WO | 01/74811 | | 10/2001 |

(Continued)

OTHER PUBLICATIONS

Gatta et al., "Synthesis of [1,2,4] Triazoloquinazoline and [1,2,4] Triazolo-1,4-benzodiazepine derivatives," Journal of Heterocyclic Chemistry, 1993, vol. 30, pp. 11-16.

(Continued)

*Primary Examiner*—Bruce Campell
*Assistant Examiner*—Michelle Horning
(74) *Attorney, Agent, or Firm*—McDonnell Boehnen Hulbert & Berghoff LLP

(57) ABSTRACT

The present invention relates to anti-HCV dihaloacetamide compounds in synergistic combination with an interferon and/or ribavirin and pharmaceutical compositions thereof for inhibition of the replication of HCV virus. The present invention also relates to the use of the compositions to inhibit HCV replication and/or proliferation and to treat or prevent HCV infections.

16 Claims, 4 Drawing Sheets

FOREIGN PATENT DOCUMENTS

Figure 1:
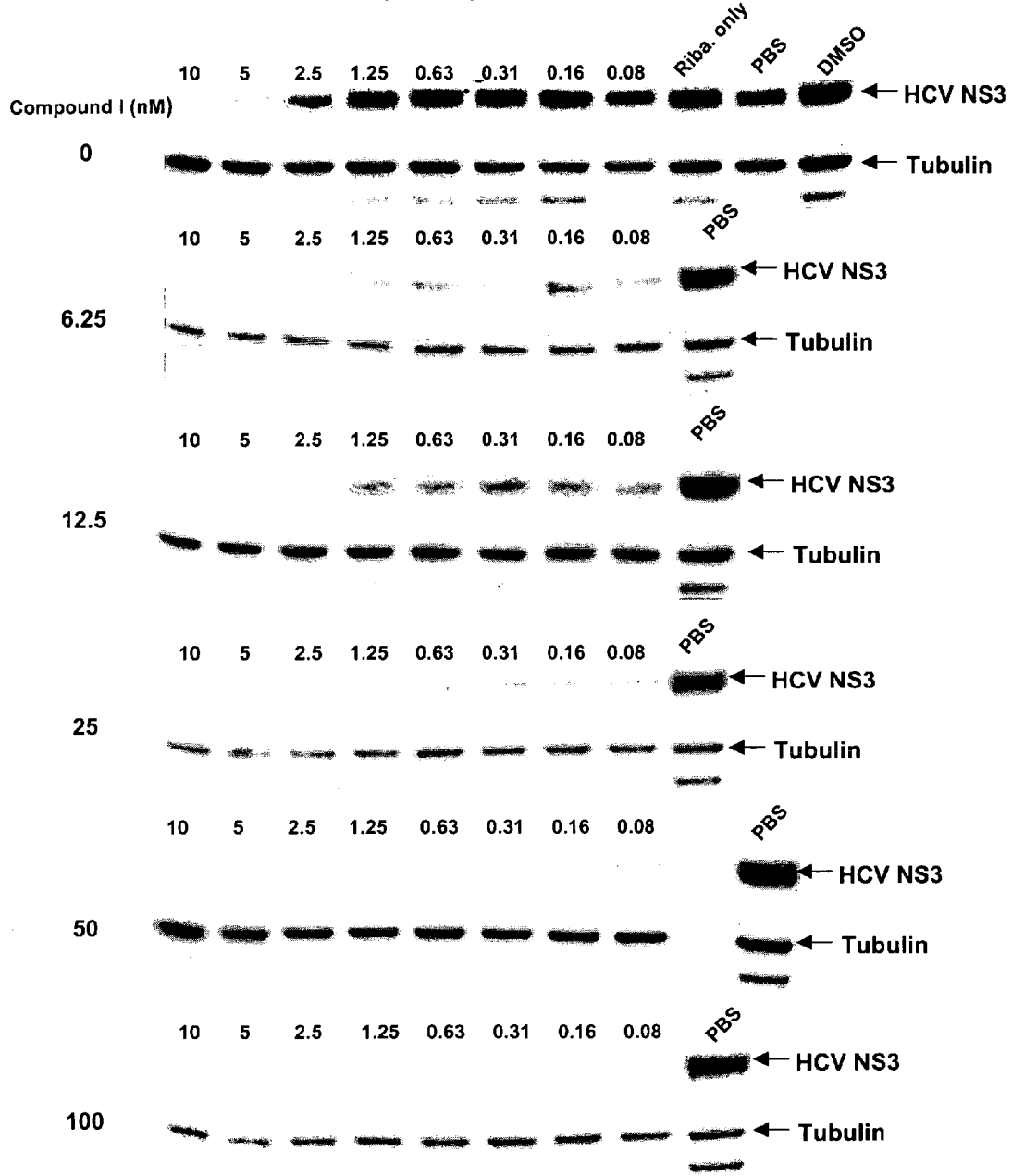

| WO | 01/78648 | 10/2001 |
|---|---|---|
| WO | 02/46186 | 6/2002 |
| WO | 02/055025 | 7/2002 |
| WO | 03/029210 | 4/2003 |
| WO | WO 03/040112 A1 | 5/2003 |
| WO | WO 2004/018463 A2 | 3/2004 |
| WO | 2004/099164 | 11/2004 |
| WO | WO 2004/099164 A1 | 11/2004 |
| WO | WO 2004/099165 A2 | 11/2004 |
| WO | WO 2004/103366 A1 | 12/2004 |
| WO | WO 2005/000308 A2 | 1/2005 |
| WO | 2005/097760 | 10/2005 |

OTHER PUBLICATIONS

Database Chemcats Online!, 1999m XP-002310049, Databased accession No. RN 247059-16-1.

Maybridge Hts, Order No. BTB 09742; RN 247059-16-1 Maybridge PLC, Trevillett, Tintagel, Cornwall, PL340HW, UK, Jan. 8, 2004, XP002297442.

STN File CA, Abstract 135:46129 & V.M. Barot et al., Asian Journal of Chemistry, 2001, 13(1), pp. 341-342.

STN File CA, Abstract 132:265141 & S.V Damie et al., Indian Journal of Heterocyclic Chemistry, 1999, 9(2), pp. 81-86.

STN File CA, Abstract 132:180505 & V.R. Naik et al., Asian Journal of Chemistry, 2000, 12(1), pp. 305-307.

STN File CA, Abstract 129:216539 & S.M. Naik et al., Oriental Journal of Chemistry, 1998, 14(1), pp. 167-168.

STN File CA, Abstract 126:74789 & M. Shah et al., Indian Journal of Chemistry, Section B: Organic Chemistry Including Medicinal Chemistry, 1996, 35B(12), pp. 1282-1286.

STN File CA, Abstract 122:81186 & S.R. Modi et al., Oriental Journal of Chemistry, 1994, 10(1), pp. 85-86.

STN File CA, Abstract 118:191597 & T. Bandiera et al., Journal of Heterocyclic Chemistry, 1992, 29(6), pp. 1423-1428.

Kanbara et al., "Preparation of Soluble and Fluorescent Polly(arylene)s by 1,3-Dipolar Polycycloaddition and Properties of the Polymers," Polymer Bulletin, vol. 36, pp. 673-679, 1996.

Ku et al., "Use of Iodoacetylene as a Dipolarphile inn the Synthesis of 5-Iodoisoxazole Derivatives," Organic Letters, vol. 3, No. 26, pp. 4185-4187, 2001.

Maybridge, plc, Trevillett, Tintagel, Catalogue No. RF01972, Cornwall PL34 OHW, England.

Maybridge, plc, Trevillett, Tintagel, Catalog No. RF01996, Cornwall PL34 OHW, England.

Gatta et al., "Synthesis of [1,2,4]Triazoloquinazoline and [1,2,4]Triazolo-1,4-benzodiazepine derivatives," Journal of Heterocyclic Chemistry, 1993, vol. 30, pp. 11-16.

Roth et al., "Zur Kondensation von Chalkonoxyden mit Hydroxylamin," Arch. Pharm., 1961, vol. 94, pp. 769-774.

Samula, "Oksymowanic Azachalkonow," Roczniki Chemll, Ann. Soc. Chim. Polonorum, 1971, vol. 45, pp. 2063.

Samula, "Cyclization of Azachalcones and B-Hydroxyketones Oximes," Roczniki Chemll, Ann soc. Chim, Polonorum, 1974, vol. 48, pp. 959-964.

Howe, et al., Nitrile Oxide Cycloaddition Routes to 2-(Isoxazoly)-benzoates and 2-(1,2,4-Oxadiazol-3-yl) benzoates, Heterocycl. Chem., 1982, vol. 19, No. 4, pp. 721-726.

Belgodere et al., "Sudies on Isomeric Pyridylisoxazoles," Heterocycles, 1983, vol. 20, No. 3, pp. 501-504.

Batori et al., "Photoinduced Rig Transformation of Pyrido [1,2-b]pyridazinium-4-olate," Tetrehedron, 1994, vol. 50, No. 16, pp. 4699-4708.

* cited by examiner

Synergistic Effect of Compound I, IFN-α, and Ribavirin on HCV Replication

FIG. 4
Quantitative Analysis of Compound I/IFN-α Synergism
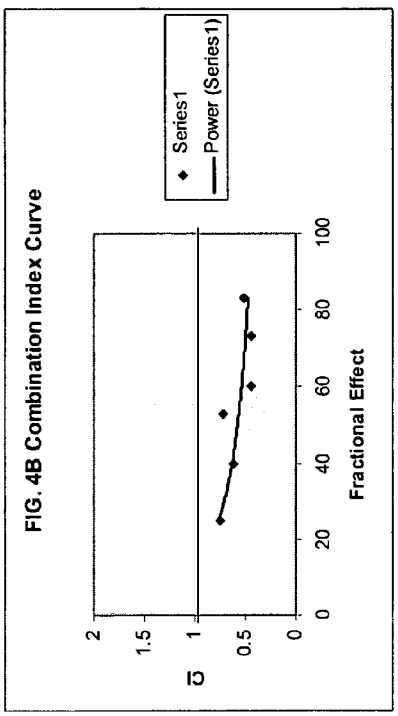
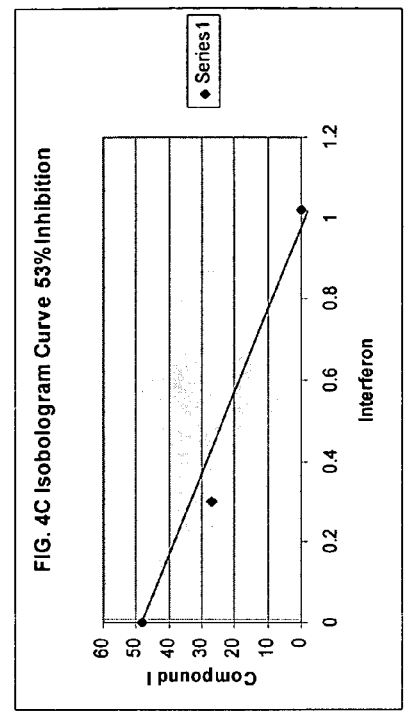
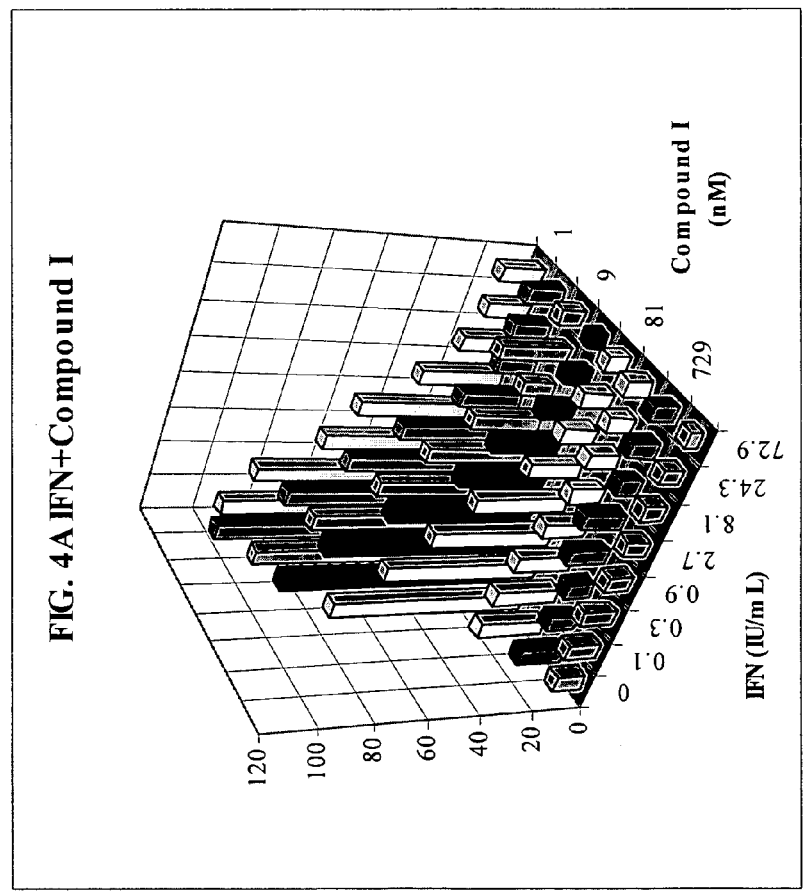

SYNERGISTICALLY EFFECTIVE COMBINATIONS OF DIHALOACETAMIDE COMPOUNDS AND INTERFERON OR RIBAVIRIN AGAINST HCV INFECTIONS

1. CROSS REFERENCE TO RELATED APPLICATION

This application claims benefit under 35 U.S.C. § 119(e) to application Ser. No. 60/523,405, filed Nov. 19, 2003, entitled "Synergistically Effective Combinations of Dihaloacetamide Compounds and Interferon or Ribavirin Against HCV Infections", the contents of which are incorporated herein in the entirety.

2. FIELD OF INVENTION

The present invention relates to anti-HCV dihaloacetamide compounds in synergistic combination with an interferon and/or ribavirin and compositions thereof. The synergistic combinations of the invention are useful for treating or preventing Hepatitis C virus (HCV) infections. In particular, the present invention relates to substituted diphenyl isoxazole, pyrazole and oxadiazole compounds and hydro isomers thereof, compositions comprising the compounds and the use of such compounds and compositions in synergistically effective amounts in combination with interferon and/or ribavirin to inhibit HCV replication and/or proliferation as a therapeutic approach towards the treatment and/or prevention of HCV infections in humans and animals.

3. BACKGROUND OF THE INVENTION

Hepatitis C virus (HCV) infection is a global human health problem with approximately 150,000 new reported cases each year in the United States alone. HCV is a single stranded RNA virus, which is the etiological agent identified in most cases of non-A, non-B post-transfusion and post-transplant hepatitis and is a common cause of acute sporadic hepatitis (Choo et al., Science 244:359, 1989; Kuo et al., Science 244:362, 1989; and Alter et al., in Current Perspective in Hepatology, p. 83, 1989). It is estimated that more than 50% of patients infected with HCV become chronically infected and 20% of those develop cirrhosis of the liver within 20 years (Davis et al., New Engl. J. Med. 321:1501, 1989; Alter et al., in Current Perspective in Hepatology, p. 83, 1989; Alter et al., New Engl. J. Med. 327:1899, 1992; and Dienstag Gastroenterology 85:430, 1983). Moreover, the only therapy available for treatment of HCV infection is interferon-α (INTRON® A, PEG-INTRON®A, Schering-Plough; ROFERON-A®, PEGASys®, Roche). Most patients are unresponsive, however, and among the responders, there is a high recurrence rate within 6-12 months after cessation of treatment (Liang et al., J. Med. Virol. 40:69, 1993).

Ribavirin, a guanosine analog with broad spectrum activity against many RNA and DNA viruses, has been shown in clinical trials to be effective against chronic HCV infection when used in combination with interferon-α (see, e.g., Poynard et al., Lancet 352:1426-1432, 1998; Reichard et al., Lancet 351:83-87, 1998), and this combination therapy has been recently approved (REBETRON, Schering-Plough; see also Fried et al., 2002, N. Engl. J. Med. 347:975-982). However, the response rate is still at or below 50%.

Ribavirin suffers from disadvantages that include, teratogenic activity, interference with sperm development, haemolysis, fatigue, headache, insomnia, nausea and/or anorexia. Interferon alpha, with or without ribavirin, is associated with many side effects. During treatment, patients must be monitored carefully for flu-like symptoms, depression, rashes and abnormal blood counts. Patients treated with interferon alpha-2b plus ribavirin should not have complications of serious liver dysfunction and such subjects are only considered for treatment of hepatitis C in carefully monitored studies.

Therefore, additional compounds for treatment and prevention of HCV infection are needed.

4. SUMMARY OF THE INVENTION

In one aspect, the present invention provides to anti-HCV dihaloacetamide compounds in synergistic combination with an interferon and/or a ribavirin. The synergistic combination(s) are potent inhibitors of Hepatitis C virus ("HCV") replication and/or proliferation.

In another aspect, the present invention provides compositions that are combinations of an anti-HCV dihaloacetamide compound in synergistic combination with an interferon and/or a ribavirin. The anti-HCV dihaloacetamide portion of the synergistic compositions generally comprise a substituted diphenyl isoxazole, pyrazole or oxadiazole, and hydro isomers thereof, as described herein, or a salt, hydrate, solvate, N-oxide or prodrug thereof and a suitable excipient, carrier or diluent. The synergistic compositions of the invention may be formulated for veterinary uses or for use in humans.

The synergistic compositions of the invention are potent inhibitors of HCV replication and/or proliferation. Accordingly, in still another aspect, the present invention provides methods of inhibiting HCV replication and/or proliferation, comprising contacting a Hepatitis C virion with an amount of a synergistic composition of the invention effective to inhibit its replication or proliferation. The methods may be practiced either in vitro or in vivo, and may be used as a therapeutic approach towards the treatment and/or prevention of HCV infections.

In a final aspect, the present invention provides methods of treating and/or preventing HCV infections. The methods generally involve administering to a subject that has an HCV infection or that is at risk of developing an HCV infection with a synergistic amount of a composition of the invention effective to treat or prevent the HCV infection. The method may be practiced in animals in veterinary contexts or in humans.

Advantageously, the synergistic combinations of the invention reach therapeutic levels faster than therapies currently available for the treatment of HCV infections. Additionally, the synergistic combination reduces the amount of either an interferon, a ribavirin, or both, thereby reducing unwanted side-effects.

5. BRIEF DESCRIPTION OF THE FIGURES

FIGS. 1-4 depict synergistic studies of Compound I with IFN-α and ribavirin.

6. DETAILED DESCRIPTION OF THE PREFERRED EMBODIMENTS

6.1 Definitions

"Adjunctively administering" means administering an anti-HCV compound(s), as described herein and either an interferon, a ribavirin, or both, to a subject in a sequence and within a time interval such that they can act together to treat, prevent, or reverse HCV infection or proliferation. For example, the therapeutic agents can be administered simultaneously in the same or separate compositions. When administered in separate compositions, a different administration mode can be used for each composition, i.e. orally and by IPE. The therapeutic agents can be administered sequentially in any order at different points in time.

"Anti-HCV dihaloacetamide compound" refers to substituted heterocycles and B-ring hydro isomers thereof according to structural formula (I), having the following "core" and numbering convention:

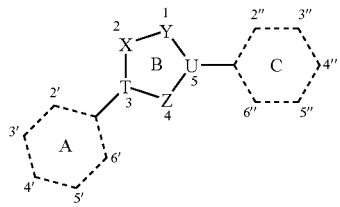

wherein the B ring is an aromatic or nonaromatic ring that includes from one to four heteroatoms. X, Y, Z are each, independently of one another selected from C, CH, N, $NR^{16}$, $NR^{18}$, S or O and U and T are each, independently of one another, selected from C, CH or N, provided that X and Y are not both O. Both of the rings "A" and "C" can be phenyl rings or, one of rings "A" or "C" can be a pyridyl ring and the other is a phenyl ring or a pyridyl ring. When "A" and/or "C" is a pyridyl, the ring may be attached to the illustrated "B" ring via any available carbon atom. Thus, the "A" and/or "C" rings may be pyrid-2-yl, pyrid-3-yl or pyrid-4-yl rings.

$R^{16}$ and $R^{18}$ are each, independently of one another, selected from the group consisting of hydrogen, lower alkyl, substituted lower alkyl, lower heteroalkyl, substituted lower heteroalkyl, cycloalkyl, substituted cycloalkyl, cycloheteroalkyl, substituted cycloheteroalkyl, lower haloalkyl, monohalomethyl, dihalomethyl, trihalomethyl, trifluoromethyl, lower alkylthio, substituted lower alkylthio, lower alkoxy, substituted lower alkoxy, methoxy, substituted methoxy, lower heteroalkoxy, substituted lower heteroalkoxy, cycloalkoxy, substituted cycloalkoxy, cycloheteroalkoxy, substituted cycloheteroalkoxy, lower haloalkoxy, monohalomethoxy, dihalomethoxy, trihalomethoxy, trifluoromethoxy, lower di- or monoalkylamino, substituted lower di- or monoalkylamino, aryl, substituted aryl, aryloxy, substituted aryloxy, phenoxy, substituted phenoxy, arylalkyl, substituted arylalkyl, arylalkyloxy, substituted arylalkyloxy, benzyl, benzyloxy, heteroaryl, substituted heteroaryl, heteroaryloxy, substituted heteroaryloxy, heteroarylalkyl, substituted heteroarylalkyl, heteroarylalkyloxy, substituted heteroarylalkyloxy, carboxyl, lower alkoxycarbonyl, substituted lower alkoxycarbonyl, aryloxycarbonyl, substituted aryloxycarbonyl, arylalkyloxycarbonyl, substituted arylalkyloxycarbonyl, carbamate, substituted carbamate, carbamoyl, substituted carbamoyl, sulfamoyl, substituted sulfamoyl and a group of the formula -L-$R^{17}$, where "L" is a linker and $R^{17}$ is cycloalkyl, substituted cycloalkyl, cycloheteroalkyl or substituted cycloheteroalkyl. The linker may be any group of atoms suitable for attaching the $R^{17}$ moiety to the nitrogen atom. Suitable linkers include, but are not limited to, moieties selected from the group consisting of —$(CH_2)_{1-6}$—, S, —C(O)—, —$SO_2$—, —NH—, —C(O)—$SO_2NH$— and combinations thereof.

The "A" ring includes a substituent positioned ortho to the point of attachment (2'- or 6'-position) and may optionally include from 1 to 4 additional substituents. The nature of the substituents can vary broadly. Typical substituent groups useful for substituting the "A" ring include halo, fluoro, chloro, alkyl, alkylthio, alkoxy, alkoxycarbonyl, arylalkyloxycarbonyl, aryloxycarbonyl, cycloheteroalkyl, carbamoyl, haloalkyl, dialkylamino or sulfamoyl groups and substituted versions thereof. In one embodiment, the "A" ring is disubstituted at the 2'- and 6'-positions and unsubstituted at all other positions.

The "C" ring can be substituted at the, ortho (2" or 6"), meta (3" or 5") or para (4") positions with a substituent of the formula —$NR^{11}C(O)R^{12}$, where $R^{11}$ is hydrogen, alkyl or methyl and $R^{12}$ is substituted alkyl, haloalkyl, dihalomethyl, dichloromethyl, cycloheteroalkyl or substituted cycloheteroalkyl. In one embodiment, $R^{12}$ is a haloalkyl, dihaloalkyl or a dichloromethyl group. The "C" ring may also be optionally substituted at one or more of the 2"-, 4"-, 5"- and/or 6"-positions with the same or different substituent groups such as those described for the "A" ring.

As will be recognized by skilled artisans, the actual electron distribution or double bonding pattern of the "B" ring will depend upon the identities of substituents X, Y, Z, T and/or U.

Suitable heterocycles include, for example, isoxazoles, pyrazoles, oxadiazoles, oxazoles, thiazoles, imidazoles, triazoles, thiadiazoles and hydro isomers thereof. Suitable hydro isomers of the afore-mentioned heterocyclic compounds include, for example, dihydro isomers as well as tetrahydro isomers. Such hydro isomers include, for example, 2-isoxazoline, 3-isoxazoline, 4-isoxazolines, isoxazolidines, 1,2-pyrazolines, 1,2-pyrazolidines, (3H)-dihydro-1,2,4-oxadiazoles, (5H)-dihydro-1,2,4-oxadiazoles, oxazolines, oxazolidines, (3H)-dihydrothiazoles, (5H)-dihydrothiazoles, thiazolidines (tetrahydrothiazoles), (3H)-dihydrotriazoles, (5H)-dihydrotriazoles, triazolidines(tetrahydrotriazoles), dihydro-oxadiazoles, tetrahydro-oxadiazoles, (3H)-dihydro-1,2,4-thiadiazoles, (5H)-dihydro-1,2,4-thiadiazoles, 1,2,4-thiadiazolidines (tetrahydrothiadiazoles), (3H)-dihydroimidazoles, (5H)-dihydroimidazoles and tetrahydroimidazoles.

A specific embodiment of anti-HCV dihaloacetamide compounds include, for example,

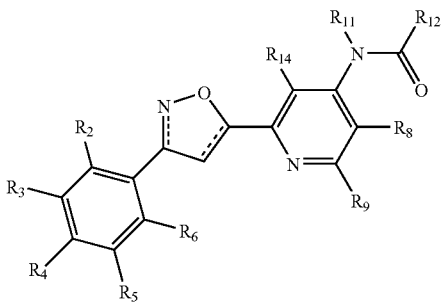

or a pharmaceutically acceptable salt, hydrate, solvate, or N-oxide thereof, wherein:

$R_2$ and $R_6$ are independently selected from the group consisting of hydrogen, halo, $C_1$-$C_{15}$ alkyl, substituted $C_1$-$C_{15}$ alkyl, $C_1$-$C_{15}$ alkylthio, substituted $C_1$-$C_{15}$ alkylthio, alkoxy, substituted alkoxy, alkoxycarbonyl, substituted alkoxycarbonyl, aryl-$C_1$-$C_{15}$ alkyloxycarbonyl, substituted aryl-$C_1$-$C_{15}$ alkyloxycarbonyl, aryloxycarbonyl, substituted aryloxycarbonyl, cycloheteroalkyl, substituted cycloheteroalkyl, carbamoyl, substituted carbamoyl, halo-$C_1$-$C_{15}$ alkyl, sulfamoyl, substituted sulfamoyl, and silyl ethers, provided that at least one of $R_2$ and $R_6$ is other than hydrogen;

$R_3$ and $R_5$ are independently selected from the group consisting of hydrogen, halo, $C_1$-$C_{15}$ alkyl, substituted $C_1$-$C_{15}$ alkyl, $C_1$-$C_{15}$ alkylthio, substituted $C_1$-$C_{15}$ alkylthio, alkoxy, substituted alkoxy, alkoxycarbonyl, substituted alkoxycarbonyl, aryl-$C_1$-$C_{15}$ alkyloxycarbonyl, substituted aryl-$C_1$-$C_{15}$ alkyloxycarbonyl, aryloxycarbonyl, substituted aryloxycarbonyl, cycloheteroalkyl, substituted cycloheteroalkyl, carbamoyl, substituted carbamoyl, halo-$C_1$-$C_{15}$ alkyl, sulfamoyl, and substituted sulfamoyl;

$R_4$ is selected from the group consisting of hydrogen, halo, $C_1$-$C_{15}$ alkyl, substituted $C_1$-$C_{15}$ alkyl, $C_1$-$C_{15}$ alkylthio, substituted $C_1$-$C_{15}$ alkylthio, carbamoyl, substituted carbamoyl, alkoxy, substituted alkoxy, alkoxycarbonyl, substituted alkoxycarbonyl, aryl-$C_1$-$C_{15}$ alkyloxycarbonyl, substituted aryl-$C_1$-$C_{15}$ alkyloxycarbonyl, aryloxycarbonyl, substituted aryloxycarbonyl, di-$C_1$-$C_{15}$ alkylamino, substituted di-$C_1$-$C_{15}$ alkylamino, halo-$C_1$-$C_{15}$ alkylamino, sulfamoyl, and substituted sulfamoyl;

$R_8$, $R_9$, and $R_{14}$ are independently selected from the group consisting of hydrogen, halo, and fluoro;

$R_{11}$ is hydrogen, or $C_1$-$C_{15}$ alkyl; and $R_{12}$ is selected from the group consisting of substituted $C_1$-$C_{15}$ alkyl, halo-$C_1$-$C_{15}$ alkyl, cycloheteroalkyl, and substituted cycloheteroalkyl.

Furthermore, the phrase "anti-HCV dihaloacetamide" is intended those compounds, hydro isomers, and positional ring isomers thereof disclosed in U.S. Pat. No. 6,759,538, issued Jul. 6, 2004 and U.S. Ser. No. 60/467,650, filed May 2, 2003, 60/467,811, filed May 2, 2003, Ser. No. 10/440,349, filed May 15, 2003, Ser. No. 10/836,561, filed Apr. 30, 2004, Ser. No. 10/838,133, filed May 3, 2004 and Ser. No. 10/646,348, filed Aug. 22, 2003 the contents of which are incorporated herein in their entirety. Specific embodiments of anti-HCV dihaloacetamide compounds include, for example,

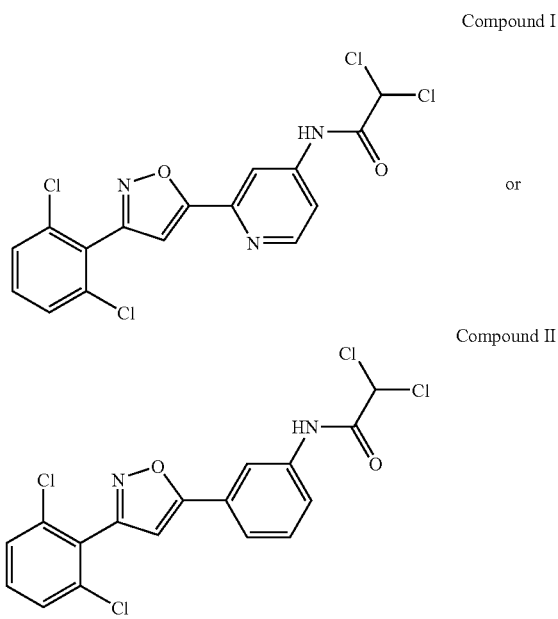

Compound I or

Compound II

"Interferon" refers to a family of naturally occurring small proteins and glycoproteins produced and secreted by most nucleated cells in response to viral infection as well as other antigenic stimuli. Interferons render cells resistant to viral infection and exhibit a wide variety of actions on cells. They exert their cellular activities by binding to specific membrane receptors on the cell surface. Once bound to the cell membrane, interferons initiate a complex sequence of intracellular events. In vitro studies demonstrate that these include the induction of certain enzymes, suppression of cell proliferation, immunomodulating activities including enhancement of the phagocytic activity of macrophages or augmentation of the specific cytotoxicity of lymphocytes for target cells, as well as inhibition of virus replication in virus-infected cells.

Furthermore, the term interferon includes the family of highly homologous species-specific proteins that inhibit viral replication and cellular proliferation and modulate immune response. Human interferons are grouped into three classes based on their cellular origin and antigenicity: α-interferon (leukocytes), β-interferon (fibroblasts) and γ-interferon (B cells). Recombinant forms of each group have been developed and are commercially available. Subtypes in each group are based on antigenic/structural characteristics. At least 24 interferon alphas (grouped into subtypes A through H) having distinct amino acid sequences have been identified by isolating and sequencing DNA encoding these peptides. The terms "α-interferon", "alpha-interferon", "interferon alpha" and "human leukocyte interferon" are used interchangeably in this application to describe members of this group. Both naturally occurring and recombinant alpha-interferons, including consensus interferon, may be used in the practice of the invention.

Typical suitable interferon-alphas include, but are not limited to, recombinant interferon alpha-2b such as Intron-A interferon available from Schering Corporation, Kenilworth, N.J., recombinant interferon alpha-2a such as Roferon interferon available from Hoffmann-La Roche, Nutley, N.J., recombinant interferon alpha-2C such as Berofor alpha 2 interferon available from Boehringer Ingelheim Pharmaceutical, Inc., Ridgefield, Conn., interferon alpha-n1, a purified blend of natural alpha interferons such as Sumiferon available from Sumitomo, Japan or as Wellferon interferon alpha-n1 (INS) available from the Glaxo-Wellcome Ltd., London, Great Britain, or a consensus alpha interferon such as those described in U.S. Pat. Nos. 4,897,471 and 4,695,623 (especially Examples 7, 8 or 9 thereof) and the specific product available from Amgen, Inc., Newbury Park, Calif., or interferon alpha-n3 a mixture of natural alpha interferons made by Interferon Sciences and available from Purdue Frederick Co., Norwalk, Conn., under the Alferon Tradename. The use of interferon alpha-2a or alpha 2b is preferred. Since interferon alpha 2b, among all interferons, has the broadest approval throughout the world for treating chronic hepatitis C infection, it is most preferred. The manufacture of interferon alpha 2b is described in U.S. Pat. No. 4,530,901, the contents of which are incorporated by reference in their entirety.

The term "interferon" is further intended to include those "pegylated" analogs meaning polyethylene glycol modified conjugates of interferon alpha, preferably interferon alpha-2a and -2b. The preferred polyethylene-glycol-interferon alpha-2b conjugate is $PEG_{12000}$-interferon alpha 2b. The phrases "12,000 molecular weight polyethylene glycol conjugated interferon alpha" and "$PEG_{12000}$-IFN alpha" as used herein mean conjugates such as are prepared according to the methods of International Application No. WO 95/13090 and containing urethane linkages between the interferon alpha-2a or -2b amino groups and polyethylene glycol having an average molecular weight of 12000, the contents of which are incorporated herein by reference in their entirety.

The preferred $PEG_{12000}$-interferon alpha-2b is prepared by attaching a PEG polymer to the epsilon amino group of a lysine residue in the IFN alpha-2b molecule. A single $PEG_{12000}$ molecule is conjugated to free amino groups on an IFN alpha-2b molecule via a urethane linkage. This conjugate is characterized by the molecular weight of $PEG_{12000}$ attached. The $PEG_{12000}$-IFN alpha-2b conjugate is formulated as a lyophilized powder for injection. The objective of conjugation of IFN alpha with PEG is to improve the delivery of the protein by significantly prolonging its plasma half-life, and thereby provide protracted activity of IFN alpha.

Other interferon alpha conjugates can be prepared by coupling an interferon alpha to a water-soluble polymer. A nonlimiting list of such polymers includes other polyalkylene oxide homopolymers such as polypropylene glycols, polyoxyethylenated polyols, copolymers thereof and block copolymers thereof. As an alternative to polyalkylene oxide-based polymers, effectively non-antigenic materials such as dextran, polyvinylpyrrolidones, polyacrylamides, polyvinyl alcohols, carbohydrate-based polymers and the like can be used. Such interferon alpha-polymer conjugates are described in U.S. Pat. No. 4,766,106, U.S. Pat. No. 4,917,888, European Patent Application No. 0 236 987, European Patent Application Nos. 0510 356, 0 593 868 and 0 809 996 (pegylated interferon alpha-2a) and International Publication No. WO 95/13090, the contents of which are incorporated herein by reference in their entirety. Additionally, U.S. Pat. Nos. 6,624,290, 6,387,365 and 5,908,621 are also incorporated herein by reference in their entirety.

"Pharmaceutically acceptable salt" refers to a salt of an anti-HCV dihaloacetamide compound of the invention which is made with counterions understood in the art to be generally acceptable for pharmaceutical uses and which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine, morpholine, piperidine, dimethylamine, diethylamine and the like. Also included are salts of amino acids such as arginates and the like, and salts of organic acids like glucurmic or galactunoric acids and the like (see, e.g., Berge et al., 1977, *J. Pharm. Sci.* 66:1-19).

"Pharmaceutically acceptable vehicle" refers to a diluent, adjuvant, excipient or carrier with which a synergistic composition of the invention is administered.

"Ribavirin" refers to 1-β-D-ribofuranosyl-1H-1,2,4-triazole-3-carboxamide, available from ICN Pharmaceuticals, Inc., Costa Mesa, Calif. and is described in the Merck Index, compound No. 8199, Eleventh Edition. Its manufacture and formulation is described in U.S. Pat. No. 4,211,771, the contents of which are incorporated herein by reference in their entirety. The term further includes derivatives or analogs thereof, such as those described in U.S. Pat. Nos. 6,063,772, 6,403,564 and 6,277,830, the contents of which are incorporated herein by reference in their entirety. For example, derivatives or analogs include modified ribavirins such as 5'-amino esters, ICN Pharmaceutical's L-enantiomer of ribavirin (ICN 17261), 2'-deoxy derivatives of ribavirin and 3-carboxamidine derivatives of ribavirin, viramidine (previously known as ribamidine) and the like.

"Synergistic" means that the therapeutic effect of an anti-HCV dihaloacetamide compound of the invention when administered in combination with an interferon and/or ribavirin, is greater than the predicted additive therapeutic effect of an anti-HCV dihaloacetamide compound of the invention, and an interferon and/or ribavirin when administered alone. Synergistic effects are known in the art and are quantitated by methods described in references such as those by Ting-Chao Chou and Paul Talalay, "Advanced Enzyme Regulation" (1984), 22: 27-55; Ting-Chao Chou and Paul Talalay, "TIPS" (1983) 450-454; and Ting-Chao Chou, Robert J. Motzer, Youzhi Tong and George J. Bosl, "Journal of the National Cancer Institute" (1994) 86: 1517-1524, the contents of which are incorporated herein by reference in their entirety.

"Synergistic combination" refers to a combination of an anti-HCV dihaloacetamide compound and either interferon, ribavirin, or both with the anti-HCV dihaloacetamide compound.

6.2 The Anti-HCV Dihaloacetamide Compounds

The invention provides substituted diphenyl heterocycle compounds (i.e., the anti-HCV dihaloacetamides) that are potent inhibitors of HCV replication and/or proliferation. In one embodiment, the compounds of the invention are substituted diphenyl isoxazoles, pyrazoles and oxadiazoles according to the teachings of U.S. Pat. No. 6,759,538, issued Jul. 6, 2004 and U.S. Ser. No. 60/467,650, filed May 2, 2003, 60/467,811, filed May 2, 2003, Ser. No. 10/440,349, filed May 15, 2003, Ser. No. 10/836,561, filed Apr. 30, 2004, Ser. No. 10/838,133, filed May 3, 2004 and Ser. No. 10/646,348, filed Aug. 22, 2003, the contents of which are incorporated herein in their entirety.

Those of skill in the art will appreciate that the synergistic anti-HCV dihaloacetamide compounds of the invention described herein may include functional groups that can be masked with progroups to create prodrugs. Such prodrugs are usually, but need not be, pharmacologically inactive until converted into their active drug form. In the prodrugs of the invention, any available functional moiety may be masked with a progroup to yield a prodrug. Myriad progroups suitable for masking such functional groups to yield promoieties that are cleavable under the desired conditions of use are known in the art.

6.3 Methods of Synthesis

Starting materials useful for preparing synergistic anti-HCV diahloacetamide compounds of the invention and intermediates thereof are commercially available or can be prepared by well-known synthetic methods (see, e.g., Harrison et al., "Compendium of Synthetic Organic Methods", Vols. 1-8 (John Wiley and Sons, 1971-1996); "Beilstein Handbook of Organic Chemistry," Beilstein Institute of Organic Chemistry, Frankfurt, Germany; Feiser et al., "Reagents for Organic Synthesis," Volumes 1-21, Wiley Interscience; Trost et al., "Comprehensive Organic Synthesis," Pergamon Press, 1991; "Theilheimer's Synthetic Methods of Organic Chemistry," Volumes 1-45, Karger, 1991; March, "Advanced Organic Chemistry," Wiley Interscience, 1991; Larock "Comprehensive Organic Transformations," VCH Publishers, 1989; Paquette, "Encyclopedia of Reagents for Organic Synthesis," 3d Edition, John Wiley & Sons, 1995). Other methods for synthesis of the compounds described herein and/or starting materials are either described in the art or will be readily apparent to the skilled artisan. Alternatives to the reagents and/or protecting may be found in the references provided above and in other compendiums well known to the skilled artisan. Guidance for selecting suitable protecting groups can be found, for example, in Greene & Wuts, "Protective Groups in Organic Synthesis," Wiley Interscience, 1999. Synthetic preparations of anti-HCV dihaloacetamide compounds useful in the present invention can be found in U.S. Pat. No. 6,759,538, issued Jul. 6, 2004 and U.S. Ser. No. 60/467,650, filed May 2, 2003, 60/467,811, filed May 2, 2003, Ser. No. 10/440,349, filed May 15, 2003, Ser. No. 10/836,561, filed Apr. 30, 2004, Ser. No. 10/838,133, filed May 3, 2004 and Ser. No. 10/646,348, filed Aug. 22, 2003, the contents of which are incorporated herein in their entirety.

6.4 Assays for Modulation of HCV

The synergistic combinations of the invention are potent inhibitors of HCV replication and/or proliferation. The activity of the synergistic combinations of the invention can be confirmed in in vitro assays suitable for measuring inhibition of viral or retroviral replication and/or proliferation. The assays may investigate any parameter that is directly or indirectly under the influence of HCV, including, but not limited to, protein-RNA binding, translation, transcription, genome replication, protein processing, viral particle formation, infectivity, viral transduction, etc. Such assays are well known in the art. Regardless of the parameter being investigated, in one embodiment, to examine the extent of inhibition, samples, cells, tissues, etc. comprising an HCV replicon or HCV RNA are treated with a potential inhibitory synergistic combination and the value for the parameter compared to control cells (untreated or treated alone with an anti-HCV dihaloacetamide, interferon and/or ribavirin, vehicle or other placebo). Control samples are assigned a relative activity value of 100%. Inhibition is achieved when the activity value of the test compound relative to the control is about 90%, preferably 50%, and more preferably 25-0%. Synergistic inhibition can be noted when the therapeutic effect of an anti-HCV dihaloacetamide compound of the invention when administered in combination with an interferon and/or ribavirin, is greater than the predicted additive therapeutic effect of an anti-HCV dihaloacetamide compound of the invention, and an interferon and/or ribavirin when administered alone.

Alternatively, the extent of inhibition may be determined based upon the $IC_{50}$ of the combination in the particular assay, as will be described in more detail, below.

In one embodiment, the inhibitory activity of the synergistic combinations can be confirmed in a replicon assay that assesses the ability of a test compound to block or inhibit HCV replication in replicon cells. One example of a suitable replicon assay is the liver cell-line Huh 7-based replicon assay described in Lohmann et al., 1999, Science 285:110-113. A specific example of this replicon assay, which utilizes luciferase translation, is provided in the Examples Section. In one embodiment of this assay, the amount of a synergistic combination that yields a 50% reduction in translation as compared to a control cell ($IC_{50}$) may be determined.

Alternatively, the inhibitory activity of the synergistic combination can be confirmed using a quantitative Western immunoblot assay utilizing antibodies specific for HCV non-structural proteins, such as NS3, NS4A NS5A and NS5B. In one embodiment of this assay, replicon cells are treated with varying concentrations of synergistic combination to determine the concentration of test synergistic combination that yields a 50% reduction in the amount of a non-structural protein produced as compared to a control sample ($IC_{50}$). A single non-structural protein may be quantified or multiple non-structural proteins may be quantified. Antibodies suitable for carrying out such immunoblot assays are available commercially (e.g., from BIODESIGN International, Saco, Me.).

Alternatively, the inhibitory activity of the synergistic combination(s) may be confirmed in an HCV infection assay, such as the HCV infection assay described in Fournier et al., 1998, J. Gen. Virol. 79(10):2367:2374, the disclosure of which is incorporated herein by reference. In one embodiment of this assay, the amount of synergistic combination that yields a 50% reduction in HCV replication or proliferation as compared to a control cell ($IC_{50}$) may be determined. The extent of HCV replication may be determined by quantifying the amount of HCV RNA present in HCV infected cells. A specific method for carrying out such an assay is provided in the Examples section.

As yet another example, the inhibitory activity of the synergistic combination can be confirmed using an assay that quantifies the amount of HCV RNA transcribed in treated replicon cells using, for example, a Taqman assay (Roche Molecular, Alameda, Calif.). In one embodiment of this assay, the amount of test synergistic combination that yields a 50% reduction in transcription of one or more HCV RNAs as compared to control samples ($IC_{50}$s) may be determined.

Regardless of the assay used, active synergistic combinations are generally those, which exhibit $IC_{50}$s in the particular assay in the range of about 1 mM or less. Synergistic combinations which exhibit lower $IC_{50}$s, for example, in the range of about 100 µM, 10 µM, 1 µM, 100 nM, 10 nM, 1 nM, or even lower, are particularly useful for as therapeutics or prophylactics to treat or prevent HCV infections.

6.5 Uses and Administration

Owing to their ability to inhibit HCV replication, the synergistic combinations of an anti-HCV dihaloacetamide and an interferon and/or a ribavirin and/or compositions thereof can be used in a variety of contexts. For example, the synergistic combinations can be used as controls in in vitro assays to identify additional more or less potent anti-HCV dihaloacetamide combinations. As another example, the synergistic combinations and/or compositions thereof can be used as preservatives or disinfectants in clinical settings to prevent medical instruments and supplies from becoming infected with HCV virus. When used in this context, the synergistic combinations and/or compositions thereof may be applied to the instrument to be disinfected at a concentration that is a multiple, for example 1×, 2×, 3×, 4×, 5× or even higher, of the measured $IC_{50}$ for the compound.

In a specific embodiment, the synergistic combinations and/or compositions can be used to "disinfect" organs for transplantation. For example, a liver or portion thereof being prepared for transplantation can be perfused with a solution comprising a synergistic combination of the invention prior to implanting the organ into the recipient. This method has proven successful with lamuvidine (3TC, Epivir®, Epivir-HB®) for reducing the incidence of hepatitis B virus (HBV) infection following liver transplant surgery/therapy. Quite interestingly, it has been found that such perfusion therapy not only protects a liver recipient free of HBV infection (HBV−) from contracting HBV from a liver received from an HBV+ donor, but it also protects a liver from an HBV− donor transplanted into an HBV+ recipient from attack by HBV. The synergistic combinations may be used in a similar manner prior to organ or liver transplantation.

The synergistic combinations and/or compositions thereof find particular use in the treatment and/or prevention of HCV infections in animals and humans. When used in this context, the synergistic combinations may be administered per se, but are typically formulated and administered in the form of a pharmaceutical composition. The exact composition will depend upon, among other things, the method of administration and will apparent to those of skill in the art. A wide variety of suitable pharmaceutical compositions are described, for example, in *Remington's Pharmaceutical Sciences*, 20th ed., 2001).

Formulations suitable for oral administration can consist of (a) liquid solutions, such as an effective amount of the active synergistic combination suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The synergistic combination of choice, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Suitable formulations for rectal administration include, for example, suppositories, which consist of the packaged nucleic acid with a suppository base. Suitable suppository bases include natural or synthetic triglycerides or paraffin hydrocarbons. In addition, it is also possible to use gelatin rectal capsules, which consist of a combination of the synergistic combination of choice with a base, including, for example, liquid triglycerides, polyethylene glycols, and paraffin hydrocarbons.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration, oral administration, subcutaneous administration and intravenous administration are the preferred methods of administration. A specific example of a suitable solution formulation may comprise from about 0.5-100 mg/ml synergistic combination and about 1000 mg/ml propylene glycol in water. Another specific example of a suitable solution formulation may comprise from about 0.5-100 mg/ml synergistic combination and from about 800-1000 mg/ml polyethylene glycol 400 (PEG 400) in water.

A specific example of a suitable suspension formulation may include from about 0.5-30 mg/ml synergistic combination and one or more excipients selected from the group consisting of: about 200 mg/ml ethanol, about 1000 mg/ml vegetable oil (e.g., corn oil), about 600-1000 mg/ml fruit juice (e.g., grapefruit juice), about 400-800 mg/ml milk, about 0.1 mg/ml carboxymethylcellulose (or microcrystalline cellulose), about 0.5 mg/ml benzyl alcohol (or a combination of benzyl alcohol and benzalkonium chloride) and about 40-50 mM buffer, pH 7 (e.g., phosphate buffer, acetate buffer or citrate buffer or, alternatively 5% dextrose may be used in place of the buffer) in water.

A specific example of a suitable liposome suspension formulation may comprise from about 0.5-30 mg/ml synergistic combination, about 100-200 mg/ml lecithin (or other phospholipid or mixture of phospholipids) and optionally about 5 mg/ml cholesterol in water. For subcutaneous administration of synergistic combination, a liposome suspension formulation including 5 mg/ml synergistic combination in water with 100 mg/ml lecithin and 5 mg/ml synergistic combination in water with 100 mg/ml lecithin and 5 mg/ml cholesterol provides good results. This formulation may be used for other synergistic combinations of the invention.

The formulations of synergistic combinations can be presented in unit-dose or multi-dose sealed containers, such as ampules and vials. Injection solutions and suspensions can be prepared from sterile powders, granules, and tablets of the kind previously described.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents, discussed in more detail, below.

In therapeutic use for the treatment of HCV infection, the synergistic combinations utilized in the pharmaceutical method of the invention are administered to patients diagnosed with HCV infection at dosage levels suitable to achieve therapeutic benefit. By therapeutic benefit is meant that the administration of a synergistic combination that leads to a beneficial effect in the patient over time. For example, therapeutic benefit is achieved when the HCV titer or load in the patient is either reduced or stops increasing. Therapeutic benefit is also achieved if the administration of synergistic combination slows or halts altogether the onset of the organ damage that or other adverse symptoms typically accompany HCV infections, regardless of the HCV titer or load in the patient.

The synergistic combinations of the invention and/or compositions thereof may also be administered prophylactically in patients who are at risk of developing HCV infection, or who have been exposed to HCV, to prevent the development of HCV infection. For example, the synergistic combinations of the invention and/or compositions thereof may be administered to hospital workers accidentally stuck with needles while working with HCV patients to lower the risk of, or avoid altogether, developing an HCV infection.

Initial dosages suitable for administration to humans may be determined from in vitro assays or animal models. For example, an initial dosage may be formulated to achieve a serum concentration that includes the $IC_{50}$ of the particular synergistic combination being administered, as measured in an in vitro assay. Alternatively, an initial dosage for humans may be based upon dosages found to be effective in animal models of HCV infection. Exemplary suitable model systems are described, for example, in Muchmore, 2001, Immunol. Rev. 183:86-93 and Lanford & Bigger, 2002, Virology, 293:

1-9, and the referenced cited therein. As one example, the initial dosage of the synergistic combination may be in the range of about 0.01 mg/kg/day to about 200 mg/kg/day, or about 0.1 mg/kg/day to about 100 mg/kg/day, or about 1 mg/kg/day to about 50 mg/kg/day, or about 10 mg/kg/day to about 50 mg/kg/day, can also be used. The dosages, however, may be varied depending upon the requirements of the patient, the severity of the condition being treated, and the synergistic combination being employed. The size of the dose also will be determined by the existence, nature, and extent of any adverse side-effects that accompany the administration of a particular synergistic combination in a particular patient. Determination of the proper dosage for a particular situation is within the skill of the practitioner. Generally, treatment is initiated with smaller dosages, which are less than the optimum dose of the synergistic combination. Thereafter, the dosage is increased by small increments until the optimum effect under circumstances is reached. For convenience, the total daily dosage may be divided and administered in portions during the day, if desired.

6.6 Combination Therapy

In certain embodiments of the present invention, the anti-HCV dihaloacetamide described throughout the specification and/or compositions thereof can be used in combination therapy with at least one other therapeutic agent. A combination of the anti-HCV dihaloacetamide and/or composition thereof and the therapeutic agent can act additively or, more preferably, synergistically. The synergistic anti-HCV dihaloacetamide and/or a composition thereof may be administered concurrently with the administration of the other therapeutic agent(s), or it may be administered prior to or subsequent to administration of the other therapeutic agent(s).

In one embodiment, the synergistic anti-HCV dihaloacetamides and/or compositions thereof are used in combination therapy with other antiviral agents or other therapies known to be effective in the treatment or prevention of HCV. As a specific example, the synergistic anti-HCV dihaloacetamides and/or compositions thereof may be used in combination with known antivirals, such as ribavirin (see, e.g., U.S. Pat. No. 4,530,901). As another specific example, the synergistic anti-HCV dihaloacetamide and/or compositions thereof may also be administered in combination with one or more of the compounds described in any of the following: U.S. Pat. No. 6,143,715; U.S. Pat. No. 6,323,180; U.S. Pat. No. 6,329,379; U.S. Pat. No. 6,329,417; U.S. Pat. No. 6,410,531; U.S. Pat. No. 6,420,380; and U.S. Pat. No. 6,448,281.

Yet another specific example, the synergistic effects of the anti-HCV dihaloacetamide and/or compositions thereof may be used in combination with interferons such as α-interferon, β-interferon and/or γ-interferon as discussed throughout the specification. For example, the interferons may be unmodified, or may be modified with moieties such as polyethylene glycol (pegylated interferons). Many suitable unpegylated and pegylated interferons are available commercially, and include, by way of example and not limitation, recombinant interferon alpha-2b such as Intron-A interferon available from Schering Corporation, Kenilworth, N.J., recombinant interferon alpha-2a such as Roferon interferon available from Hoffmann-La Roche, Nutley, N.J., recombinant interferon alpha-2C such as Berofor alpha 2 interferon available from Boehringer Ingelheim Pharmaceutical, Inc., Ridgefield, Conn., interferon alpha-n1, a purified blend of natural alpha interferons such as Sumiferon available from Sumitomo, Japan or as Wellferon interferon alpha-n1 (INS) available from the Glaxo-Wellcome Ltd., London, Great Britain, or a consensus alpha interferon such as those described in U.S. Pat. Nos. 4,897,471 and 4,695,623 (especially Examples 7, 8 or 9 thereof) and the specific product available from Amgen, Inc., Newbury Park, Calif., or interferon alpha-n3 a mixture of natural alpha interferons made by Interferon Sciences and available from the Purdue Frederick Co., Norwalk, Conn., under the Alferon Tradename, pegylated interferon-2b available from Schering Corporation, Kenilworth, N.J. under the tradename PEG-Intron A and pegylated interferon-2a available from Hoffman-LaRoche, Nutley, N.J. under the tradename Pegasys.

As yet another specific example, the synergistic anti-HCV dihaloacetamides of the invention and/or compositions thereof may be administered in combination with both a ribovirin and an interferon.

7. EXAMPLES

The following examples are provided by way of illustration only and not by way of limitation. Those of skill in the art will readily recognize a variety of noncritical parameters that could be changed or modified to yield essentially similar results.

7.1 Anti-HCV Dihaloacetamide Compound Syntheses

Exemplary preparations of the anti-HCV dihaloacetamide compounds, hydro isomers, and positional ring isomers thereof are disclosed in U.S. Pat. No. 6,759,538, issued Jul. 6, 2004 and U.S. Ser. No. 60/467,650, filed May 2, 2003, 60/467,811, filed May 2, 2003, Ser. No. 10/440,349, filed May 15, 2003, Ser. No. 10/836,561, filed Apr. 30, 2004, Ser. No. 10/838,133, filed May 3, 2004 and Ser. No. 10/646,348, filed Aug. 22, 2003, the contents of which are incorporated herein in their entirety. Those having ordinary skill in the art can prepare such compounds provided by these teachings as well as those described throughout the present application.

7.2 Exemplary Synergistic Combinations of the Invention Inhibit HCV Translation or Replication 7.2.1 Replicon Assay The inhibitory activity of certain exemplary synergistic combination of the invention can be confirmed using an HCV replicon assay. The HCV replicon can include such features as the HCV 5' untranslated region including the HCV IRES, the HCV 3' untranslated region, selected HCV genes encoding HCV polypeptides, selectable markers, and a reporter gene such as luciferase, GFP, etc. In the assay, actively dividing 5-2 Luc replicon-comprising cells (obtained from Rolf Bartenschlager; see Lohmann et al., 1999, Science 285:110-113) can be seeded at a density of between about 5,000 and 7,500 cells/well onto 96 well plates (about 90 µl of cells per well) and incubated at 37° C. and 5% $CO_2$ for 24 hours. Then, the test synergistic combination (in a volume of about 10 µl) can be added to the wells at various concentrations and the cells can be incubated for an additional 24 hours before luciferase assay. The media can be aspirated from each well and Bright-Glo (Promega, Madison, Wis.) luciferase assay reagents can be added to each well according to the manufacturer's instructions. Briefly, the Bright-Glo reagent can be diluted 1:1 with PBS and 100 µl of diluted reagent can be added to each well. After 5 min of incubation at room temperature, luciferin emission can be quantified with a luminometer. In this assay, the amount of test synergistic combination that yields a 50% reduction in luciferase emission ($IC_{50}$) can be determined.

7.2.2 Western Blot Assay

Certain exemplary synergistic combinations of the invention can also be tested for their ability to inhibit HCV replication using a quantitative Western blot analysis with antibodies specific for the HCV nonstructural protein NS3.

Actively dividing 9-13 replicon cells can be seeded into 6-well plates at a density of $1\times10^5$ cells/well in a volume of 2 ml/well and can be incubated at 37° C. and 5% $CO_2$ for 24 hours. Various concentrations of test compounds (in a volume of 10 ul) were can be added to the wells and the cells can be incubated for another 48 hours. Protein samples can be prepared from the cultured cells, then could be resolved on a SDS-PAGE gel and then could be transferred to a nitrocellulose membrane. The membrane can be blocked with 5% non-fat milk in PBS for 1 hour at room temperature. Primary antibody (anti NS3 antibody; Rigel Pharmaceuticals, South San Francisco, Calif.) incubation can be performed for 1 hour at room temperature, after which the membrane can be washed 3 times (for 15 min per time) with PBST (PBS plus 0.1% Tween 20). Horseradish peroxidase conjugated secondary antibody incubation can be performed for 1 hour at room temperature and the membrane can be washed 3 times (for 15 min per time) with PBST. The membrane can then be soaked in substrate solution (Pierce) and can then be exposed to a film or quantified using an imager. In this assay, the amount of test synergetic combination that yields a 50% reduction in the amount of NS3 protein translated as compared to a control sample ($IC_{50}$) can be determined.

FIGS. 1 through 4 depict dose studies of compound I in combination with IFNα and ribavirin as determined by HCV NS3 and tubulin responses. FIG. 1 shows the relative reduction of NS3 versus tubulin protein production in replicon cells under varying concentrations of interferon-α, varying concentrations of compound I, and a constant concentration of Ribavirin. It should be noted that HCV NS3 is not eliminated by the combination of interferon-α and ribavirin in the absence of compound I.

Figure 2:
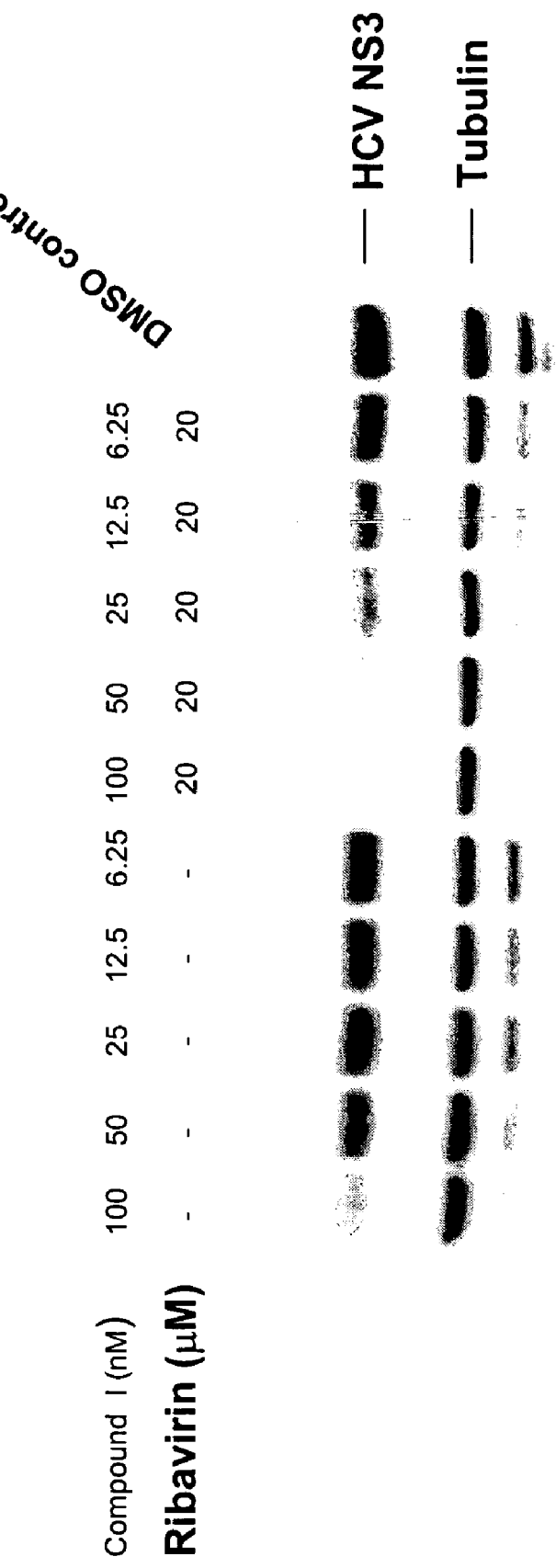

FIG. 2 shows the synergy between compound I and ribavirin, wherein ribavirin is held at a constant concentration and the concentration of compound I is varied. At a concentration of 100 nM of compound I and 20 μm ribavirin, HCV NSD is eliminated while β-tublin remained unchanged.

Figure 3:
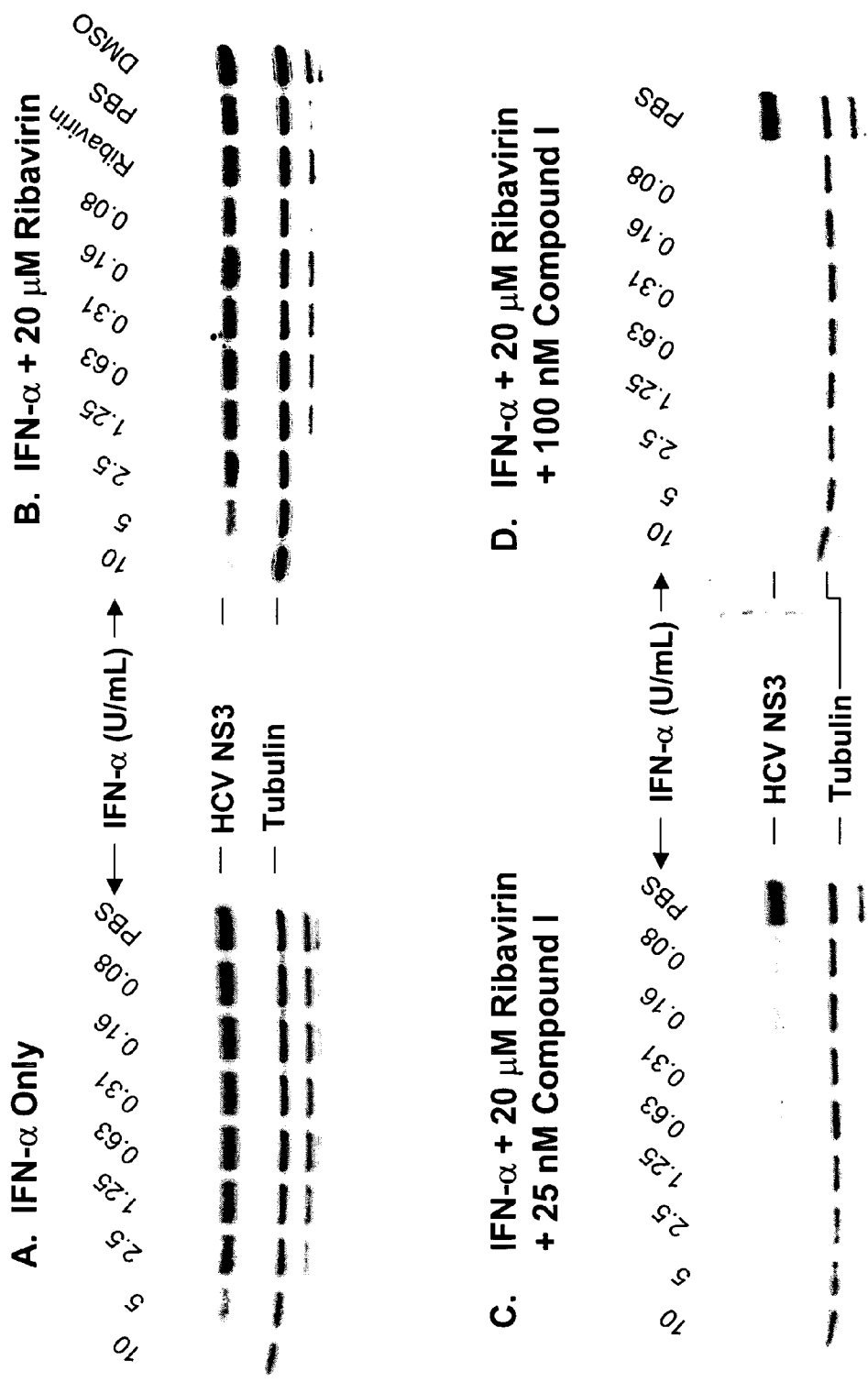

FIG. 3 depicts the synergistic effects of compound I, interferon-α, and ribavirin on HCV replication. FIG. 3(a) demonstrates that interferon-α at elevated concentrations becomes effective against HCV replication, as indicated by the reduction of HCV NS3 in replicon cells. FIG. 3(b) shows that the combination of interferon-α and ribavirin is about equally as effective as interferon-α alone. FIGS. 3(c) and 3(d) demonstrate that with increasing concentrations of compound I, in combination with interferon-α and ribavirin, effectively eliminates HCV NS3.

FIG. 4A depicts the synergistic effects between Compound 1, interferon-α and ribavirin. In FIG. 4B, values below 1 demonstrate synergistic effects from the combination of components. In FIG. 4C, points or values below the straight line also demonstrate synergistic activity.

To determine synergism between interferon-α and anti-HCV dihaloacetamide compounds, the following protocol was utilized. A cell culture was prepared with HCV replicon cells plated at a desirable density (e.g. $2\times20^4$ cells per well) in a 96-well format 24 hour prior to compound treatment. The effect of a test anti-HCV dihaloacetamide and IFN-α combination treatment on the replicon was examined by a two-factor dose titration, i.e., by varying the amounts of both IFN-α (0, 0.2, 0.67, 2, 6, 18, 54 IU/mL) and test anti-HCV dihaloacetamide (0, 5, 15, 45, 135, 405, 1215 μM). The cells were washed with PBS three days after the treatment. The effectiveness of the treatment was determined by analyzing the level of HCV driven luciderase gene expression. Quantitation of synergistic effect of interferon-α and test anti-HCV dihaloacetamide were determined. The data from the combination treatment were subjected to synergism assessment using established methods (i.e., Finch et al., Blood, 96(6): 2262-2268; Taladay et al., Adv. Enzyme Regul. 1984; 22: 27-55; Tallarida, R. J., J. Pharm. Expt. Ther. 2001; 398: 865-872) the contents of which are incorporated herein by reference in their entirety.

7.2.3 Luciferase Counter Screen

A counter screen can be used to identify non-specific inhibitors of the luciferase reporter gene. In the counter screen, a cell line carrying a construct such as a CMV-driven luciferase gene can be used to identify compounds that inhibit the reporter gene, and not HCV. In these CMV-Luc cells, the DNA construct, which comprises a luciferase gene downstream of a CMV promoter, is permanently integrated into the chromosome of Huh7 cells. For the counter screen, actively dividing CMV-Luc cells can be seeded at a density of 5000-7500 cells/well in a volume of 90 ul/well into 96 well plate(s). The cells can be then incubated at 37° C. and 5% $CO_2$ for 24 hours. Various concentrations of test synergistic combinations (in a volume of 10 ul) can be added to the wells and the cells can be incubated for another 24 hours. Media can be aspirated from each well and Bright-Glo (Pharmacia) luciferase assay reagents can be added to each well according to the manufacturer's manual. Luciferin counts can be taken using a luminometer.

7.2.4 HCV Infection Assay

The activity of synergistic combinations of the invention can also be confirmed in an HCV infection assay. The assay can be carried out essentially as described in Fournier et al., 1998, J. Gen. Virol. 79:2367-2374. Briefly, hepatocyte cells from a donor can be plated on Day 1. On Day 3, the cells can be inoculated with HCV virus and test synergistic combination compound would be added. On Day 5, the medium can be changed and test synergistic combination would be added. On Day 7, the medium would be changed and test synergistic combination would be added. On Day 8, the RNA would be isolated and the HCV RNA could be quantified using a Taqman assay.

7.3 The Synergistic Combinations can be Non-Toxic in Cellular and Animal Models 7.3.1 Cytotoxicity Synergistic combinations of the invention can be tested in a cytotoxicity assay with liver cells including an HCV replicon (5-2 Luc cells, 9-13 cells or Huh-7 cells). In the assay, cells can be seeded onto 96-well plates (approx. 7500 cells/well in a volume of 90 μl) and grown for 24 hr at 37° C. On day 2, various concentrations of synergistic test combinations (in a volume of 10 μl) can be added to the wells and the cells can be grown for an additional 24 hr at 37° C. On day 3, an ATP-dependent R-Luciferase assay (Cell Titer Glo assay) can be performed to determine the number of viable cells.

7.4 Sustained Plasma Levels can be Achieved

The pharmacokinetic properties of synergistic combinations of the invention can be calculated in rats, monkeys and chimpanzees using the intravenous and subcutaneous routes of administration with a variety of different delivery vehicles. Sustained plasma levels can be achieved with several different liposome suspension vehicles using subcutaneous administration: for example, (i) 5 mg/ml synergistic combination in water with 100 mg/ml lecithin; (ii) 5 mg/ml synergistic combination in water with 200 mg/ml lecithin; and (iii) 5 mg/ml synergistic combination in water with 100 mg/ml lecithin and 5 mg/ml cholesterol. Based on these results, it is expected that other liposome formulations as are well-known in the art may be used to administer the synergistic combinations of the invention.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

What is claimed is:

1. A method of treating an HCV infection comprising adjunctively administering to a subject a synergistically effective amount of a combination comprising an anti-HCV dihaloacetamide compound with an interferon and/or a ribavirin.

2. The method of claim 1 in which the interferon is an alpha-interferon.

3. The method of claim 2 in which the alpha interferon is IFNα-1a or IFNα-1b.

4. The method of claim 1 in which the interferon is interferon alpha-n1 (INS).

5. The method of claim 1 in which the interferon is β-interferon or an ω-interferon.

6. The method of claim 1 in which the interferon comprises a pegylated interferon.

7. The method of claim 6 in which the pegylated interferon is pegylated interferon-2b, pegylated interferon-2a or a combination thereof.

8. The method of claim 1 in which the ribavirin has the structure 1-β-D-ribofuranosyl-1,2,4-triazole.

9. The method of claim 1 in which the combination includes both the interferon and the ribavirin.

10. The method of any one of claims 1-9 in which the anti-HCV dihaloacetamide compound is compound I:

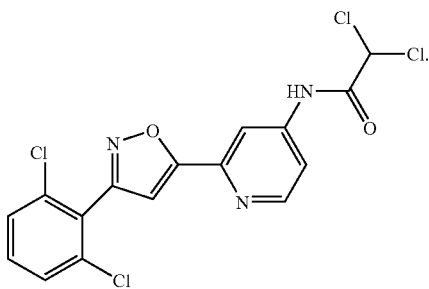

11. The method of any one of claims 1-9 in which the anti-HCV dihaloacetamide compound is compound II:

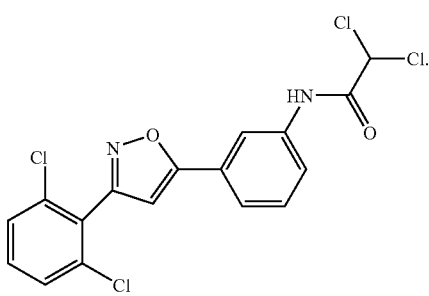

12. The method of any one of claims 1-9 in which the anti-HCV dihaloacetamide compound is a mixture of compound I:

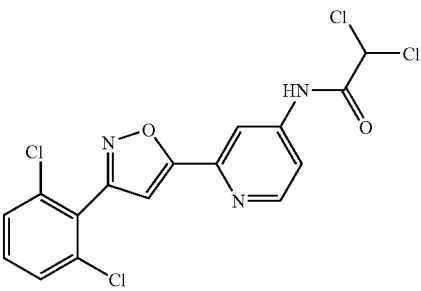

and compound II:

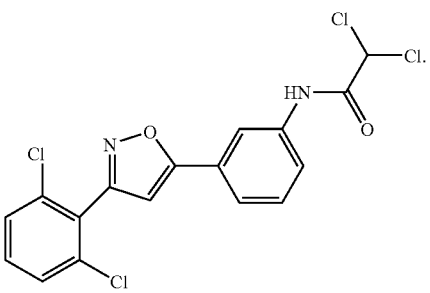

13. The method of claim 1 in which the anti-HCV dihaloacetamide compound, interferon and/or ribavirin are administered simultaneously.

14. The method of claim 1 in which the anti-HCV dihaloacetamide compound, interferon and/or ribavirin are administered sequentially in any order.

15. A method of inhibiting HCV replication comprising contacting an HCV virion with a synergistically effective combination comprising an anti-HCV dihaloacetamide compound, an interferon and/or a ribavirin.

16. The method of claim 1 wherein the anti-HCV dihaloacetamide compound is of the following structural formula:

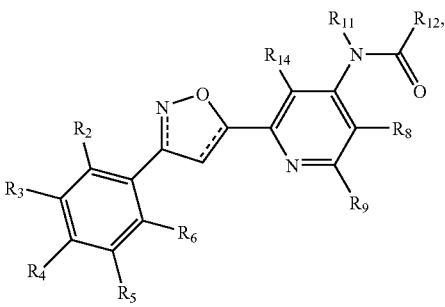

or a pharmaceutically acceptable salt, hydrate, solvate, or N-oxide thereof, wherein:

$R_2$ and $R_6$ are independently selected from the group consisting of hydrogen, halo, $C_1$-$C_{15}$ alkyl, substituted $C_1$-$C_{15}$ alkyl, $C_1$-$C_{15}$ alkylthio, substituted $C_1$-$C_{15}$ alkylthio, alkoxy, substituted alkoxy, alkoxycarbonyl, substituted alkoxycarbonyl, aryl-$C_1$-$C_{15}$ alkyloxycarbonyl, substituted aryl-$C_1$-$C_{15}$ alkyloxycarbonyl, aryloxycarbonyl, substituted aryloxycarbonyl, cycloheteroalkyl, substituted cycloheteroalkyl, carbamoyl, substituted carbamoyl, halo-$C_1$-$C_{15}$ alkyl, sulfamoyl, substituted sulfamoyl, and silyl ethers, provided that at least one of $R_2$ and $R_6$ is other than hydrogen;

$R_3$ and $R_5$ are independently selected from the group consisting of hydrogen, halo, $C_1$-$C_{15}$ alkyl, substituted $C_1$-$C_{15}$ alkyl, $C_1$-$C_{15}$ alkylthio, substituted $C_1$-$C_{15}$ alkylthio, alkoxy, substituted alkoxy, alkoxycarbonyl, substituted alkoxycarbonyl, aryl-$C_1$-$C_{15}$ alkyloxycarbonyl, substituted aryl-$C_1$-$C_{15}$ alkyloxycarbonyl, aryloxycarbonyl, substituted aryloxycarbonyl, cycloheteroalkyl, substituted cycloheteroalkyl, carbamoyl, substituted carbamoyl, halo-$C_1$-$C_{15}$ alkyl, sulfamoyl, and substituted sulfamoyl;

$R_4$ is selected from the group consisting of hydrogen, halo, $C_1$-$C_{15}$ alkyl, substituted $C_1$-$C_{15}$ alkyl, $C_1$-$C_{15}$ alkylthio, substituted $C_1$-$C_{15}$ alkylthio, carbamoyl, substituted carbamoyl, alkoxy, substituted alkoxy, alkoxycarbonyl, substituted alkoxycarbonyl, aryl-$C_1$-$C_{15}$ alkyloxycarbonyl, substituted aryl-$C_1$-$C_{15}$ alkyloxycarbonyl, aryloxycarbonyl, substituted aryloxycarbonyl, di-$C_1$-$C_{15}$ alkylamino, substituted di-$C_1$-$C_{15}$ alkylamino, halo-$C_1$-$C_{15}$ alkylamino, sulfamoyl, and substituted sulfamoyl;

$R_8$, $R_9$, and $R_{14}$ are independently selected from the group consisting of hydrogen, halo, and fluoro;

$R_{11}$ is hydrogen, or $C_1$-$C_{15}$ alkyl; and $R_{12}$ is selected from the group consisting of substituted $C_1$-$C_{15}$ alkyl, halo-$C_1$-$C_{15}$ alkyl, cycloheteroalkyl, and substituted cycloheteroalkyl.

* * * * *